United States Patent [19]

Morton

[11] Patent Number: 5,102,867

[45] Date of Patent: * Apr. 7, 1992

[54] THERAPEUTIC TREATMENT OF ABNORMAL CELL GROWTH WITH FOLLICLE REGULATORY PROTEIN

[75] Inventor: Donald L. Morton, Pacific Palisades, Calif.

[73] Assignee: Decatur-FRP/Partners, Los Angeles, Calif.

[*] Notice: The portion of the term of this patent subsequent to Jul. 18, 2006 has been disclaimed.

[21] Appl. No.: 379,995

[22] Filed: Jul. 14, 1989

Related U.S. Application Data

[63] Continuation-in-part of Ser. No. 915,074, Oct. 3, 1986, Pat. No. 4,849,402.

[51] Int. Cl.⁵ .................... A61K 37/43; A61K 35/54; C07K 15/06
[52] U.S. Cl. ........................................ 514/2; 514/21; 424/559; 530/853
[58] Field of Search ...................... 514/2, 21; 424/105, 424/559; 530/853

[56] References Cited

U.S. PATENT DOCUMENTS

| | | | |
|---|---|---|---|
| 4,734,398 | 3/1988 | diZerega | 514/2 |
| 4,764,502 | 8/1988 | diZerega | 514/2 |

OTHER PUBLICATIONS

Moore, Chem. Abstracts, vol. 83 (1975): 145343n.
Fujimori et al. Biological Abstracts, 82:33083 (1986).

*Primary Examiner*—Jacqueline Stone
*Attorney, Agent, or Firm*—Pretty, Schroeder, Brueggemann & Clark

[57] ABSTRACT

A method of treating a patient exhibiting a neoplasm is provided comprising administering a therapeutically effective dose of Follicle Regulatory Protein (FRP), or a polypeptide analog thereof. The method may be used both pre- and post-operatively.

17 Claims, No Drawings

THERAPEUTIC TREATMENT OF ABNORMAL CELL GROWTH WITH FOLLICLE REGULATORY PROTEIN

This application is a continuation-in-part of U.S Ser. No. 915,074 filed Oct. 3, 1986 now U.S. Pat. No. 4,849,402.

BACKGROUND OF THE INVENTION

The immense complexity of higher organisms requires extremely sensitive and sophisticated systems for regulating and integrating such processes as, for example, growth, regeneration, reproduction, and metabolic rate. Hormones are chemical messengers which play a crucial role in such regulation. Generally synthesized by specialized parts of the body called endocrine glands, they are carried throughout the body in the circulating blood and evoke specific responses in distant targeted tissues and organs. Human reproduction is a prime example of an extremely complex and highly integrated system finely coordinated by a set of interactive hormones. The nature and function of hormones which act on this system are continually being elucidated.

Recently, a previously unknown hormone termed Follicle Regulatory Protein, or FRP, has been identified. FRP is a protein secreted by the granulosal cells of the ovary which affects such reproductive functions in mammals as the production of sex hormones, growth and development of gametes, and ovulation. Unlike other hormones secreted by the reproductive organs, such as estrogen, which indirectly affect reproductive function by stimulating or inhibiting release of other hormones by endocrine organs such as the pituitary, it appears that FRP directly affects adjacent reproductive cells and tissues. FRP has been demonstrated to inhibit the maturation of ovarian follicles in females and spermatogenesis in males. FRP appears to be primarily responsible for the fact that in certain species, such as man, where single births are the norm, only one egg matures in the ovaries per menstrual or estrus cycle. Thus, FRP appears to have an important role in regulating the activity of normal reproductive cells.

The uncontrolled cell growth known as cancer causes about 20% of the premature deaths in the Western Hemisphere. Among the 950,000 cases of malignancy in the U.S. occurring in 1988, almost 90% were carcinomas or sarcomas (lung, breast, colon and prostate, etc.). The human reproductive tract is subject to numerous types of cancers, many of which are difficult to detect and carry a high mortality rate. Two of the most common are ovarian and testicular cancers which result from neoplasms of gonadal cells; together such cancers will account for some 12,000 projected deaths in the United States in 1986.

Surgical removal and chemotherapy are currently the only effective treatment for most reproductive malignancies. However, because many tumors are internal, such cancers often remain undetected until the tumor has grown and spread to such an extent that surgical correction is ineffective of impossible. Chemotherapy, while potentially effective in some cases, has limited activity in most patients and is associated with considerable toxicity and undesirable side effects resulting from the wide ranging effects of such treatment.

There thus remains a long-felt need for a method of treating abnormal cell growth which is effective and carries few side effects. The present invention satisfies these needs and provides other related advantages as well.

SUMMARY OF THE INVENTION

The present invention involves a novel method for treating abnormal cell growths. The method is effective in lessening the growth of cancer cells where the malignancy is detected early and, in addition, may be used post-operatively to prevent recurrence or spread of the tumor. The method is of particular utility in that it has few side effects and avoids the use of potentially toxic chemotherapeutic agents.

According to one aspect of the invention, there is provided a method of treating neoplasms comprising administering FRP in therapeutically effective doses whereby growth of cancer cells is slowed. Such treatments are administered intravenously, interperitoneally, or intramuscularly, and may be repeated at intervals. In another aspect of the invention, FRP is administered as an adjunct to surgical therapy during the post-operative period to inhibit the growth of any neoplastic cells remaining in the body after surgery.

It will be appreciated from the foregoing that the present invention provides a novel treatment for malignancies which have been heretofore difficult to control or eliminate. Other features and advantages of the present invention will become apparent from the following more detailed description, which illustrates, by way of example, the principles of the invention.

DETAILED DESCRIPTION OF THE INVENTION

FRP, a hormone produced by the granulosal cells of the ovary, inhibits normal maturation of ovarian follicle and spermatogenesis. As chemical messengers, hormones exert their effect on appropriate tissues by binding to specific receptor sites located on the surfaces of targeted cells. Such binding then sets into motion a complex cycle of molecular events resulting in an evoked response by the targeted tissue. Normally, only a limited number of cell types will express a receptor to any one hormone, thus resulting in the specificity of the hormonal effect. Moreover, many hormones produce a cascade of effects by stimulating or inhibiting cells of other endocrine glands, thus quantitatively or qualitatively changing the composition of hormones in the circulating blood.

FRP exerts a direct effect on certain normal cells of the female reproductive systems, such as the granulosal cells of the ovary. Unexpectedly, however, administration of FRP has been discovered to have an inhibitory effect on neoplastic growth and maturation of other cell types. Thus, according to the present invention, therapeutic treatment with FRP provides an effective and safe method of lessening the tumor burden in malignancies. Moreover, as an adjunct to operative removal of the tumor mass, FRP administration inhibits growth of any remaining neoplastic cells.

FRP, which may be recovered from the follicular fluid of certain mammals, such as pigs, mice, monkeys, and humans, or may be chemically synthesized, is diluted with a physiologically acceptable solution, such as phosphate buffered saline (PBS). The solution is then administered in therapeutically effective doses interperitoneally, intramuscularly, or, preferably, intravenously. Treatments are repeated at intervals as necessary to effect a retardation of neoplastic cell growth in cases where surgical removal of the tumor is not indicated. Alternatively, such an FRP solution is administered post-operatively at regular intervals to inhibit regrowth of any remaining cancerous cells.

The present invention provides a method of therapeutically or post-operatively treating a patient exhibiting a neoplasm or having had a neoplasm removed, comprising administering a therapeutically effective dose of Follicle Regulatory Protein (FRP), or a polypeptide analog thereof having substantially the same amino acid sequence and the activity of naturally occurring FRP, to said patient. Thus modifications in FRP which retain the essential function of FRP are contemplated. Preferably the therapeutically effective dose is about 50 to 500 mg/M$^2$ of patient body surface/day of pure FRP and is determined through a chemosensitivity assay utilizing cells derived from the patient's neoplasm. The neoplasm can be of non-gonadal origin, especially a sarcoma or a melanoma, for example lung, breast, uterine and colon.

The therapeutic treatment with FRP can utilize any type of administration including intramuscular injection and intravenous infusion. Any effective treatment regimen can be utilized and readily determined and repeated as necessary to effect treatment.

EXAMPLE I

PREPARATION OF FOLLICLE REGULATORY PROTEIN (FRP)

FRP was prepared from porcine follicular fluid according to the method of Ono, et al., 1986, Am. J. Obstet. Gynecol. 154:709, which is incorporated by reference. Briefly, porcine follicular fluid was repeatedly extracted with ammonium sulfate. The 0% to 35% saturated ammonium sulfate extract was percolated through a gel column containing dye matrix gel orange A equilibrated with the buffer consisting of 0.02 mol/liter Tris pH 7.5 Bound fractions were eluted with the equilibration buffer plus 0.5 mol/liter potassium chloride. Fractions containing activity as determined by aromatase inhibition, as detailed in Ono, supra, were pooled, dialyzed against distilled water and lyophilized.

The material was further purified through anion-exchange chromatography using a Mono Q Column. Fractions containing FRP were injected on a Mono P hydrogen ion - exchange column and eluted fractions exhibiting FRP activity were further purified by preparative scale gel-exclusion chromatography on a Spherogel TSK G30000SWG Column fitted to a Waters high performance liquid chromatograph. Resulting samples were reduced by ultrafiltration (Amicon Diaflow system with PM 10 membranes). Samples with FRP activity were used in subsequent examples.

FRP isolated and purified in this way was found to be approximately 5% pure. Thus 100 mg of solution contains approximately 5 mg of pure FRP. Unless otherwise indicated, for the purposes of the following examples, amounts of FRP used will be provided in terms of a solution having a purity of 5%. However, this amount can be easily converted to an approximate equivalent of pure FRP by multiplying by 0.05. Where used, the term "pure FRP" shall mean the equivalent of essentially 100% pure FRP.

The FRP so isolated and purified was lyophilized and stored in glass vials at room temperature. When ready for use, the lyophilized FRP was dissolved in Roswell Park Memorial Institute Tissue Culture Media Number 1640 (hereinafter "RPMI 1640"), in a concentration of 0.5 to 400 µg/ml.

EXAMPLE II

PREPARATION OF TISSUE SAMPLES

Human tumor tissues were obtained from individuals surgically treated for ovarian, breast, uterine, lung, colon or testicular cancer as well as sarcomas and melanomas. Viable-appearing, non-necrotic tissue was selected from surgically resected tumors, and adipose and connective tissue removed. The tissue was minced into pieces less than two millimeters in diameter in the presence of RPMI 1640 containing 15% heat-inactivated fetal calf serum (Flow Laboratories, McLean, Va.).

EXAMPLE III

PREPARATION OF SINGLE CELL SUSPENSIONS FROM TUMOR BIOPSY AND TISSUE CULTURE CELL LINES

Ten to 20 ml of enzyme media consisting of RPMI 1640 containing 0.01% DNAase (500 Kunitz units per ml; Sigma Chemical Company, St. Louis, Mo.) and 0.14% collagenase Type I (Sigma) were added per gram of tumor fragment. The mixture was stirred for 90 minutes at 37° in the presence of 5% $CO_2$. After enzymatic digestion, the free cells were decanted through 12 layers of sterile gauze and centrifuged at 200 ×g for 10 minutes. The supernatant was removed, cells were resuspended in RPMI 1640 and viability determined by trypan blue exclusion. The cells were centrifuged again and the cell pellet resuspended in RPMI 1640 containing 15% fetal calf serum and 10% dimethylsulphoxide (DMSO) in which the cells were placed in a screw cap vial in a program freezer and cooled at one degree per minute for storage at liquid nitrogen temperatures.

When established cell lines were tested in the assay, single cell suspensions were made by resuspension of monolayer cultures of the cell lines by treatment with 0.25% trypsin in RPMI 1640.

EXAMPLE IV

FRP TREATMENT OF CELL SUSPENSION

Ampules of the tumor cells were removed from the liquid nitrogen freezer, thawed in a 37° C. water bath, placed in a centrifuged tube, and spun at 200 ×g for 10 minutes. The supernatant was removed and the cells were resuspended in RPMI 1640 containing 15% fetal calf serum, after which they were placed in an incubator at 37° C. containing 5% $CO_2$ and allowed to recover overnight. The next day, the cells were washed four times in RPMI 1640 with 300 mg glutamine 1.

Cell viability was determined by trypan blue exclusion and using 0.05% trypan blue in phosphate buffered saline. Eighty thousand cells were placed in test tubes and centrifuged at 200 ×g for 10 minutes. The serum-free media was removed and each sample was then resuspended in 100 lambda of RPMI 1640 containing the particular concentration of FRP being tested. The cells and FRP mixture were incubated for two hours at 37° C.

EXAMPLE V

CHEMOSENSITIVITY ASSAY

Cells, from both biopsy and established cell lines, were cultured on an underlayer of 0.5% agarose (Sea-Plaque, FMS Corporation, Rockland, ME), which was prepared by mixing 3.5 ml molten 3% agarose with 16.5 ml RPMI 1640 supplemented with 5% heat-inactivated fetal calf serum, 2mM L-glutamine (GIBCO, (Grand Island Biological Company) Grand Island, N.Y.), 100 units/ml penicillin, 100 μ/ml streptomycin, and 1.25 μg/ml fungizone. One-half ml of this agarose mixture was added to each 16×18 mm well of 24-well plates (Costar 3524, Costar, Cambridge, Mass.), and the plates were refrigerated for 10 minutes at 4° C. Cells were suspended in 0.6% agarose in RPMI 1640 supplemented with antibiotics and 15% fetal calf serum as above. One-half ml of the cell suspension was added to each of three under-layers at a final concentration of 80,000 cells/well.

FRP purified as described in Example I was added to samples as an overlayer in 300 μL of RPMI 1640, in concentrations of 0.5 to 400 μg/well. Controls were prepared as above with FRP omitted from the overlayer. After 48 hours incubation at 37° C., 5 μCi of tritiated thymidine (specific activity 2.0 Ci/mM, New England Nuclear, Boston, Mass.) were layered over each well, and the plates were returned to the incubator for an additional 48 hours. Incorporation of thymidine was terminated by transferring the agarose layers from each well to 15 ml centrifuge tubes (No. C3051-870, Beral Scientific, Arleta, Calif.) and boiling the tubes for 15 minutes in a water bath. The volume was brought up to 13 ml with phosphate buffered saline (PBS) (GIBCO) and the tubes were centrifuged; pellets were washed with PBS and then dissolved in 3 ml of 0.85 N KOH for one hour at 80° C. Tubes were cooled on ice to below 4° C. and the hydrolysates were precipitated by the addition of 30 μl of 1% human serum albumin (Cutter Biological, Berkeley, Calif.) and 2.4 ml of ice-cold 30% trichloroacetic acid (TCA). After overnight storage at 4° C., the precipitates were collected by centrifugation. The pellets were washed with 4% trichloroacetic acid, dissolved in 0.3 mil of 0.075 N KOH, and transferred to scintillation vials containing 5 ml Liquiscint (National Diagnostics, Somerville, N.J.). Radioactivity in each vial was measured in a Beckman liquid scintillation counter (LS230, Beckman Instruments, Irvine, Calif.). An assay was considered evaluable if the average count of the untreated (no FRP) controls was greater than 300 cpm. Cell suspensions were treated and assayed. Inhibition of a cell growth was measured by comparing the number of counts in the tubes exposed to FRP to the controlled tubes exposed to RPMI 1640 alone.

EXAMPLE VI

EFFECT OF FRP TREATMENT ON OVARIAN ADENOCARCINOMA CELLS

Table I shows the results of chemosensitive assays on the adenocarcinomas and melanomas at varying concentrations of FRP. FRP was found to cause inhibition of cell growth as measured by inhibition of thymidine uptake against four out of five ovarian adenocarcinomas tested. In duplicate experiments, activity was found at 25 μg per dose against adenocarcinoma Sample Nos. 1, 2, 3, and 4, at 5 μg per dose activity was seen against adenocarcinoma #1 and minor activity against adenocarcinoma Sample No. 4. No significant activity was found at 0.5 mg against any of the ovarian adenocarcinomas. When FRP was tested at higher concentrations of 40 to 400 μg, no inhibition was seen at higher concentrations of FRP shown on Table I except it was still active at 40 μg per ml.

TABLE I

% INHIBITION OF THYMIDINE UPTAKE TYPE OF MALIGNANCY

| FRP DOSE | MELA-NOMA | ADENOCAR-CINOMA #1 | #2 | #3 | #4 | #5 |
|---|---|---|---|---|---|---|
| 400 μg | | 0 (64%) | | | | |
| 200 μg | | 0 (41%) | | | | |
| 100 μg | | 0 (57%) | | | | |
| 40 μg | | 40% | | | | |
| 25 μg | 0 | 46% | 22% | 22% | 16% | 0/0 |
| 20 μg | 0 | 23%/27%* | | | | |
| 5 μg | 0 | 25%/23%* | 0% | 0 | 6% | 0/0 |
| 0.5 μg | 0 | 0/0 | 0% | 0 | 2% | 0/0 |

*Results reflect duplicate experiments performed at different times utilizing the same methodology.

EXAMPLE VII

EFFECT OF FRP TREATMENT ON SEMINOMA

FRP was tested against testicular cancer (seminoma) at a dose of 25 μg, 5 μg, and 0.5 μg per ml. Human testicular cancer was very sensitive as seen in Table II to FRP. Fifty-one percent inhibition was observed at the dose of 25 μg FRP per ml. Significant inhibition was also observed at a concentration of 0.5 μg per ml. Inhibition curves for testicular cancer suggest that there is a portion of the testicular carcinoma population of cells that are very sensitive to inhibition by FRP.

TABLE II

INHIBITION OF TESTICULAR CANCER BY FRP (SEMINOMA)

| DOSE | % INHIBITION |
|---|---|
| 25 μg | 51 |
| 5 μg | 40 |
| 0.5 μg | 46 |

EXAMPLE VIII

THERAPEUTIC TREATMENT OF RECURRENT OVARIAN MALIGNANCY WITH FRP

Patients exhibiting recurrent ovarian cancer and those demonstrating metastasis of ovarian cancer beyond the abdominal cavity are treated with FRP to retard tumor cell growth. FRP is prepared from mammalian follicular fluid according to the method of Example I. Alternatively, it can be immunopurified, chemically synthesized or produced by recombinant DNA technology utilizing methods well known in the art. From the lyophilized state, FRP is dissolved in an appropriate physiologically acceptable carrier such as PBS.

Patients are treated by intramuscular injection or continuous intravenous infusion of FRP in an appropriate physiologically acceptable solution. The appropriate dosage will be determined by assaying the effect of FRP at varying levels upon the growth of samples of malignant gonadal tissues according to the chemosensitivity assay detailed in Example VII. An appropriate dose will be administered which is effective to provide the serum levels of FRP which are found to cause maximum inhibition of neoplastic growth in chemosensitivity assay. The proper dose, which varies according to such factors as the particular type of neoplasm, the renal function of the patient, menopausal state of the patient, general condition of health of the patient, and species of origin of the FRP, generally ranges between about 50 and 500 mg FRP/$m_2$ of body surface/day.

After a thirty-day period, the effect of FRP on the growth rate of the metastatic measurable tumor is evaluated. If the tumor is stable in size or has decreased in size, the therapeutic regime is continued until there is evidence of tumor progression based upon standard clinical criteria utilizing physical examination, diagnostic x-rays, radionucleotide scans and other appropriate diagnostic tests.

EXAMPLE IX

POST-OPERATIVE TREATMENT WITH FRP

Patients who have been previously treated by surgical reduction of their tumor burden and have no gross evidence of tumor remaining following surgery are placed on a maintenance program of continuous daily intramuscular injections of FRP at a dose of 50 to 500 mg/M$^2$ of body surface/day. This dose of FRP is continued for up to about two years, or until there is evidence of tumor regrowth and progression, as detected by standard clinical criteria.

EXAMPLE X

TREATMENT ON BREAST HUMAN TUMOR BIOPSY AND CELL LINES

FRP was tested against human breast tumor biopsies. Doses of 0.1 to 25 mg/ml were tested. 20% or greater inhibition was observed at the doses of 0.5 mg/ml to 25 mg/ml. FRP was purified as in Example I. Results are shown in Table III.

EXAMPLE XI

EFFECT OF FRP TREATMENT ON UTERINE HUMAN TUMOR BIOPSY

FRP was tested against human uterine biopsies. Doses of 0.1 to 25 mg/ml were tested. 20% or greater inhibition was observed at the doses of 0.5 mg/ml to 25 mg/ml. FRP was purified as in Example I. Results are shown in Table III.

EXAMPLE XII

EFFECT OF FRP TREATMENT ON SARCOMA BIOPSY AND CELL LINES

FRP was tested against human sarcoma biopsies. Doses of 0.1 to 25 mg/ml were tested. 20% or greater inhibition was observed at the doses of 0.5 mg/ml to 25 mg/ml. FRP was purified as in Example I. Results are shown in Table III.

EXAMPLE XIII

EFFECT OF FRP TREATMENT ON ADDITIONAL TESTES HUMAN TUMOR BIOPSIES

FRP was tested against human testes biopsies. Doses of 0.1 to 25 mg/ml were tested. 20% or greater inhibition was observed at the doses of 0.5 mg/ml to 25 mg/ml. FRP was purified as in Example I. Results are shown in Table III.

EXAMPLE XIV

EFFECT OF FRP TREATMENT ON LUNG HUMAN TUMOR BIOPSY

FRP was tested against human lung biopsies. Doses of 0.1 to 25 mg/ml were tested. 20% or greater inhibition was observed at the dose of 0.5 mg/ml to 25 mg/ml. FRP was purified as in Example I. Results are shown in Table III.

EXAMPLE XV

EFFECT OF FRP TREATMENT ON COLON HUMAN TUMOR BIOPSY

FRP was tested against human colon biopsies. Doses of 0.1 to 25 mg/ml were tested. 20% or greater inhibition was observed at the doses 0.5 mg/ml to 25 mg/ml. FRP was purified as in Example I. Results are shown in Table III.

EXAMPLE XVI

EFFECT OF FRP TREATMENT ON ADDITIONAL MELANOMA BIOPSIES

FRP was tested against human melanoma biopsies. Doses of 0.1 to 25 mg/ml were tested. 20% or greater inhibition was observed at the doses 0.5 mg/ml to 25 mg/ml. FRP was purified as in Example I. Results are shown in Table III.

TABLE III

| | POS./TOTAL | MEAN INHIBITION |
|---|---|---|
| | | BIOPSY |
| Ovarian | 6/9 | 32% |
| Breast | 3/6 | 40% |
| Uterine | 2/3 | 30% |
| Sarcoma | 2/4 | 39% |
| Testis | 1/1 | 51% |
| Lung | 3/3 | 45% |
| Colon | 1/1 | 70% |
| Melanoma | 9/14 | 41% |
| TOTAL | 27/41 = 66% | 43% |
| | | CELL LINES |
| Ovarian | 1/1 | 66% |
| Breast | 1/4 | 48% |
| Sarcoma | 1/1 | 45% |
| Melanoma | 2/7 | 37% |
| TOTAL | 5/13 = 39% | 49% |

Although the invention has been described with reference to the presently preferred embodiment, it should be understood that various modifications can be made without department from the spirit of the invention. Accordingly, the invention is limited only by the following claims.

What is claimed is:

1. A method of therapeutically treating a patient exhibiting a neoplasm comprising administering a therapeutically effective dose of Follicle Regulatory Protein (FRP), or a polypeptide analog thereof having substantially the same amino acid sequence and the activity of naturally occurring FRP, to said patient, wherein said neoplasm is ovarian adenocarcinoma, seminoma, breast tumor, uterine tumor, sarcoma, testes tumor, lung tumor, colon tumor or melanoma.

2. The method of claim 1 wherein said therapeutically effective dose is about 50 to 500 mg/M$^2$ of patient body surface/day of pure FRP.

3. The method of claim 1 wherein said therapeutically effective dose is determined through a chemosensitivity assay utilizing cells derived from the patient's neoplasm 4. The method of claim 1 wherein said neoplasm is selected from the group consisting of a sarcoma and a melanoma.

5. The method of claim 1 wherein said neoplasm is a tumor selected from the group consisting of lung, breast, uterine and colon.

6. The method of claim 1 wherein said therapeutic treatment further comprises intramuscular injection of FRP.

7. The method of claim 1 wherein said therapeutic treatment further comprises continuous intravenous infusion of FRP.

8. The method of claim 1 wherein said therapeutic treatment is repeated as necessary to effect treatment.

9. The method of claim 1 wherein the neoplasm is a nongonadal origin.

10. A method of post-operatively treating a patient having previously had a neoplasm surgically removed, comprising administering a therapeutically effective dose of FRP, or a polypeptide analog thereof having substantially the same amino acid sequence and the activity of naturally occurring FRP, to said patient, wherein said neoplasm is ovarian adenocarcinoma, seminoma, breast tumor, uterine tumor, sarcoma, testes tumor, lung tumor, colon tumor or melanoma.

11. The method of claim 10 wherein said therapeutically effective dose is about 50 to 500 mc/$M^2$ of patient body surface/day of pure FRP.

12. The method of claim 10 wherein said therapeutically effective dose of FRP is determined through a chemosensitivity assay utilizing cells derived from the patient's neoplasm.

13. The method of claim 10 wherein said neoplasm is selected from the group consisting of a sarcoma and a melanoma.

14. The method of claim 10 wherein said neoplasm is a tumor selected from the group consisting of lung, breast, uterine or colon.

15. The method of claim 10 wherein said therapeutic treatment further comprises intramuscular injection of FRP.

16. The method of claim 10 wherein said therapeutic treatment further comprises continuous intravenous infusion of FRP.

17. The method of claim 10 wherein said therapeutic treatment is repeated as necessary to effect treatment.

* * * * *

UNITED STATES PATENT AND TRADEMARK OFFICE
CERTIFICATE OF CORRECTION

PATENT NO. : 5,102,867
DATED : April 7, 1992
INVENTOR(S) : Donald L. Morton It is certified that error appears in the above-identified patent and that said Letters Patent is hereby corrected as shown below:

In column 1, line 62, please delete "correction is ineffective of impossible" and insert therefore --correction is ineffective or impossible--.

In column 5, line 2, please delete "supplemented with 5%" and insert therefore --supplemented with 15%--.

In column 7, line 24, please delete "TREATMENT ON BREAST HUMAN TUMOR BIOPSY AND CELL LINES" and insert therefore --EFFECT OF FRP TREATMENT ON BREAST HUMAN TUMOR BIOPSY AND CELL LINES--.

Signed and Sealed this

Thirtieth Day of August, 1994

*Attest:*

BRUCE LEHMAN

*Attesting Officer*   *Commissioner of Patents and Trademarks*